8/8/78

OR  4,105,888

United States Patent [19]
Fey

[11] 4,105,888
[45] Aug. 8, 1978

[54] ARC HEATER APPARATUS FOR PRODUCING ACETYLENE FROM HEAVY HYDROCARBONS

[75] Inventor: Maurice G. Fey, Plum Borough, Pa.

[73] Assignee: Westinghouse Electric Corp., Pittsburgh, Pa.

[21] Appl. No.: 703,740

[22] Filed: Jul. 9, 1976

[51] Int. Cl.² .............................................. H05B 7/18
[52] U.S. Cl. .................. 219/121 P; 219/75; 313/231.4; 75/11
[58] Field of Search .................. 75/10 R, 11; 219/75, 219/121 P, 383; 313/231.4

[56] References Cited

U.S. PATENT DOCUMENTS

| 3,554,715 | 1/1971 | Bruning et al. | 219/121 P X |
| 3,765,870 | 10/1973 | Fey et al. | 75/10 R |
| 3,849,584 | 11/1974 | Paton et al. | 219/121 P X |

Primary Examiner—Arthur T. Grimley
Assistant Examiner—M. Paschall
Attorney, Agent, or Firm—L. P. Johns

[57] ABSTRACT

Arc heater apparatus and method for producing acetylene from heavy hydrocarbons characterized by arc heater means for producing arc heated plasma gas forming a downstream reaction zone, wall means forming a plenum chamber having a substantially vertical axis and surrounding the reaction zone, inlet means upstream of the arc heated plasma gas for introducing heavy hydrocarbons into the chamber, and the walls of the chamber flaring downwardly outwardly to minimize the deposit of solid reaction products on the walls.

3 Claims, 2 Drawing Figures

ARC HEATER APPARATUS FOR PRODUCING ACETYLENE FROM HEAVY HYDROCARBONS

BACKGROUND OF THE INVENTION

1. Field of the Invention

This invention relates to electric arc heater apparatus and method and, more particularly, it pertains to such apparatus for the production of acetylene from heavy hydrocarbons such as coal and liquid or gaseous petroleum feedstock.

2. Description of the Prior Art

Acetylene produced from coal is becoming economically more attractive as the prices of light hydrocarbon feedstocks increase. A principal use for acetylene would be in the production of vinyl chloride which is presently produced from ethylene. Acetylene can be substituted for ethylene for a large number of additional processes. From the technical studies performed by several independent sources on the production of acetylene from coal, it appears that this process is close to being economically competitive with ethylene in the production of several intermediate products.

In one study the arc heater used was powered with a water cooled metal anode and either a carbon or water cooled metal cathode. The arc was rotated by means of an axial magnetic field, the source of which was a DC coil around the tubular shaped arc heater. The coal fed into the arc heater dropped through this rotating arc that might be idealized as a spoke in a wheel as it rotates around the center electrode. As the coal and gas go through the arc, they rapidly reach temperatures of from about 2000° to well above 4000° K. At these temperatures acetylene is the most prevalent of the pyrolysis products. If the high temperature acetylene were cooled slowly to the temperature range of 600° to 1200° K, it would readily decompose into less valuable products. So it is necessary for the high temperature gaseous products in the arc to be rapidly quenched to temperatures below 600° K to avoid any decomposition of the acetylene.

To quench the exit gas, pulverized coal, hydrogen, or recycled hydrocarbon liquid or gas from the process is introduced into the stream and mixed with it thoroughly, thus dropping the temperature to below 600° K. This rapid quenching minimizes the decomposition of the acetylene. After quenching, the gases are processed to separate the different valuable components such as char, carbon black, ethylene, cyanide, and other chemicals all of which are commercially desirable products. By using a rotating radial DC arc, the principal problem was the formation of deposits on the arc heater wall. These deposits consisted of a hard carbon crust that was not easily removed. To prevent the formation of the larger crust very frequent washes with steam or water were required to remove these deposits in their finely divided state, before they could form a larger crust. In their operation they were required to shut down power and the coal and gas feeds every minute for a three second wash. The overall effect on production time in this mode of operation would be significantly greater than the three seconds stated due to lags in startup and shutdown. This washing operation not only caused a lower productivity for a given power arc heater but it also meant that there was an additional capital expense for power and control equipment, and higher operating costs due to increased utilities as well as maintenance.

SUMMARY OF THE INVENTION

It has been found in accordance with this invention that the foregoing problem may be overcome by providing arc heater apparatus comprising walls forming a plenum chamber having a substantially vertical axis, three arc heaters at the upper end of the plenum chamber and extending radially outwardly from the vertical axis, each arc heater including a pair of axially spaced substantially cylindrical electrodes forming a narrow gap therebetween and adapted to be connected to a source of potential to produce an arc therebetween, the electrodes defining an arc chamber that communicates with the plenum chamber, gas inlet means communicating with the gap for introducing a non-conductive reducing gas into the arc chamber, the arc heater is being productive of an arc heated plasma gas to effect a downstream reaction zone in the plenum chamber, second inlet means upstream of the arc heater for introducing heavy hydrocarbon material such as coal and liquid or gaseous petroleum feedstocks, into the reaction zone, the walls forming the plenum chamber diverging downwardly and outwardly from the location of the arc heater, whereby any deposit of solid reaction product on the walls drop from the walls after attaining a certain thickness.

The invention is also characterized by a process for the production of acetylene from heavy hydrocarbons comprising the steps of providing three radially disposed electric arc heaters, striking an electric arc in an axial gap between generally hollow, cylindrical electrodes spaced along a common axis which forms an arc chamber in each electric arc heater, passing a reducing gas selected from at least one of a group consisting of hydrogen, carbon monoxide, and methane, forcefully through the gap into each arc chamber to produce an arc heated plasma jet while forming a downstream reaction zone, containing the reaction zone in a plenum chamber with which each arc chamber communicates and which has a substantially vertical axis and downwardly, outwardly tapered walls, and feeding into the plenum chamber and upstream of the reaction zone a stream of heavy hydrocarbon material, such as coal and/or liquid or gaseous petroleum to effect a reaction between said material and said gas to produce acetylene gas.

The advantage of the device of this invention is that a three phase arc heater structure is provided and is capable of performing the acetylene synthesis without graphite deposits forming in areas that would interfere with the rotation of the arc.

DESCRIPTION OF THE PREFERRED EMBODIMENT

In accordance with this invention, the process is carried out in the following sequential manner:

(1) striking an electric arc in an axial gap between generally hollow, cylindrical electrodes spaced along a common axis which form a chamber in at least one electric arc heater, (2) passing a reducing gas of at least one of a group consisting of hydrogen, carbon monoxide, and methane, forcefully through the gap into the chamber to produce an arc heated plasma jet while forming a downstream reaction zone, (3) containing the reaction zone in a plenum chamber having a substantially vertical axis and downwardly, outwardly tapered walls, and (4) feeding into the plenum chamber and upstream of the reaction zone a stream of heavy hydrocarbon material, such as coal, liquid petroleum, or coal tar distillates, to effect a reaction between said material and said gas to produce acetylene gas.

Figure 2:
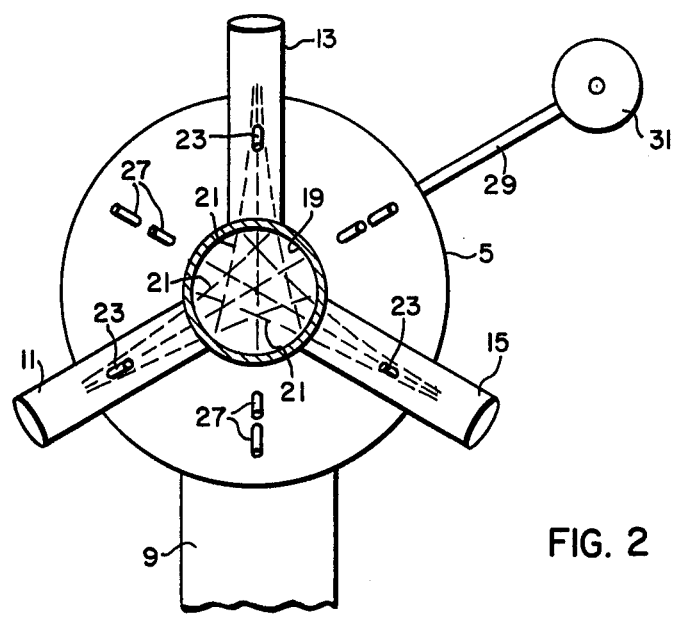
FIG. 2 is a horizontal sectional view taken on the line II—II of FIG. 1.
Figure 1:
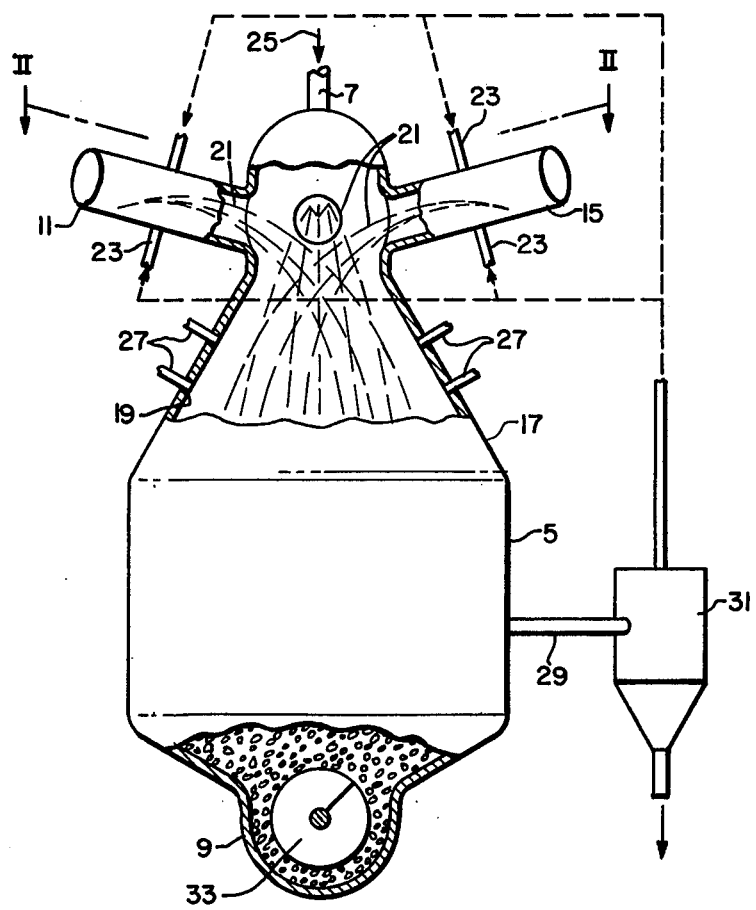
FIG. 1 is a diagrammatic view of an arc heater structure characterizing the apparatus and process of this invention.

The process of this invention may be carried out in a structure characterized by that shown in FIG. 1 in which a reactor or collecting vessel 5 is provided with an inlet 7 at the upper end and an outlet 9 at the lower end. Arc heater means including at least one and preferably three arc heaters 11, 13, 15 (FIG. 2) are provided at the upper end of the structure. The vessel 5 is composed of a suitable material, such as metal, the upper end of which includes a tapered portion 17 having downwardly and outwardly extending wall means which encloses a plenum chamber having a substantially vertical axis. The exit ends of the arc heaters 11, 13, (FIG. 2) communicate with the plenum chamber 19 so that similar plasma jet streams 21 extend from each of the arc heaters into the plenum chamber.

The arc heaters 11, 13, 15 are similar in construction and operation to that disclosed in U.S. Pat. No. 3,765,870, entitled "Method Of Direct Or Reduction Using A Short Gap Arc Heater" of which the inventors are Maurice G. Fey and George A. Kemeney, which is incorporated by reference herein. Because of the full disclosure in that patent, the description of the arc heaters 11, 13, 15 is limited herein to the basic structure and operation. The arc heaters 11, 13, 15 are each a single phase, self-stabilizing AC structures capable of power levels up to about 3500 kilowatts or up to about 10,000 kilowatts for a three phase plant installation as disclosed. In the practice of this invention it is preferred that three arc heaters be provided, one for each of the three phases of the AC power supply. Two arc heaters 11, 15 are shown in FIG. 1.

During operation of the arc heaters 11, 13, 15 a non-conductive reducing gas, such as a hydrocarbon gas selected from a group consisting of hydrogen, carbon monoxide, and methane, is introduced into the arc heaters through peripherally disposed inlet 23 which gas comprises a greater portion of the plasma jet stream 21 that enter the plenum chamber 19.

The feedstock 25 comprises liquid petroleum or finely divided coal and is introduced into the plenum chamber 19 through the inlet 7. The feedstock 25 enters the plasma jet stream 21 where, in the presence of the reducing gas (methane), it is reduced to acetylene gas. As shown in FIG. 1 the three arc heaters project radially outwardly from a vertical axis of the plenum chamber 19 and are preferably inclined upwardly at an angle in order to facilitate the direction of the plasma jet stream 21 downwardly into the plenum chamber 19. As the feedstock, such as pulverized coal, is introduced at the top of the plenum chamber, it falls through the chamber and encounters the arc or plasma jets 21 as well as the hot gases leaving the three arc heaters. The relatively high velocity emission from the arc heaters prevents solids or liquid in the plenum chamber from entering the chambers of the arc heaters and following the arc initiating gaps or arcing surfaces of the electrodes, whereby the arc heaters are capable of performing the acetylene synthesis without graphite deposits forming in the areas that would interfere with rotation of the arc within each arc heater.

It is desirable that the upstream electrodes of the arc heaters 11, 13, 15 be located close enough to the plenum chamber 19 so that in actual operation the jets or arcs 21 from the three arc heaters make contact with each other within the plenum chamber. Thus, the arc path is between the three upstream electrodes of the arc heaters with arc conduction through the impingement point of the plasma jet streams 21. In this mode of operation only the upstream electrode of the arc heaters are subjected to arc wear. The arc heating of the feedstock materials is efficient because most of the heating occurs within the path of the feedstock being admitted to the plenum chamber 19.

In accordance with this invention the outwardly flared or tapered portion 17 of the reactor vessel 5 avoids the buildup of carbon or char on the chamber walls. Whatever buildup of char or other material occurs on the wall of the chamber is not seriously detrimental to the process. For instance, where after a certain period of operation the buildup may interfere with normal operation, limited amounts of water or steam may be injected into the plenum chamber to remove the buildup. With this design of the arc heater structure it is not necessary to shut off the power, and normal operation resumes in a matter of seconds.

By providing the outwardly tapered wall portion 17 however at a suitable angle, thick wall deposits will be discharged automatically by falling from the wall to the lower end of the reactor vessel 5 due to a gradual buildup in thickness of the deposits. To expedite the automatic discharge, however, a plurality of spaced ports 27 may be added to the tapered portion 17 to apply high pressure gas, steam, or water periodically to remove thin deposits.

The reaction between the feedstock material, such as coal and liquid petroleum, with a reductant gas, such as methane ($CH_4$), is complex and not susceptible to simple formulation. The feedstock and reductant gas merely act as heat transfer agents and disassociate to effect the pyrolysis and rapid formation of acetylene.

The resulting gaseous products including carbon black, acetylene, hydrogen, carbon monoxide, and several hydrocarbons resulting from that pyrolysis, are removed from the vessel 5 through an outlet conduit 29 which conduit passes through a cyclone particle separator 31. The gases are then either partially or totally returned to the inlet 23 for recirculation through the arc heater apparatus. As validified material, such as char and carbon, collect at the bottom of the vessel, it may be withdrawn through the outlet 9 in any suitable manner such as by a screw conveyor 33.

In conclusion, the foregoing apparatus and process is specifically suited for the production of acetylene from coal and liquid petroleum feedstocks directly from an arc heated type of heat.

What is claimed is:

1. Arc heater apparatus for producing acetylene from heavy hydrocarbon, comprising walls forming a plenum chamber having a substantially vertical axis, a plurality of arc heaters at the upper end of the chamber and including a pair of axially spaced substantially cylindrical electrodes forming a narrow gap therebetween and adapted to be connected to a source of potential to produce an arc therebetween, the electrodes defining an arc chamber that communicates with the plenum chamber, the axes of the arc chambers of the arc heaters being inclined upwardly from the vertical axis, gas inlet means communicating with the gap for introducing a non-conductive reducing gas into the arc chamber, the arc heaters being productive of an arc heated plasma gas to effect a downstream reaction zone in a plenum chamber, second inlet means upstream of the arc heaters for introducing heavy hydrocarbon material into the reaction zone, and the walls forming the plenum chamber diverging downwardly and outwardly from the location of the arc heaters so that deposits of solid reaction products on the walls are minimized.

2. The apparatus of claim 1 in which there are three arc heaters at the upper end of the plenum chamber and extending radially outwardly from the vertical axis.

3. The apparatus of claim 2 in which there are a series of ports in the plenum chamber walls for the introduction of pressurized fluid to remove any buildup of deposits.

* * * * *